(12) United States Patent
Horan et al.

(10) Patent No.: US 9,375,220 B2
(45) Date of Patent: *Jun. 28, 2016

(54) JIG AND SAW GUIDES FOR USE IN OSTEOTOMIES

(71) Applicant: DePuy Synthes Products, LLC, Raynham, MA (US)

(72) Inventors: Timothy J. Horan, Royersford, PA (US); Christopher H. Scholl, West Chester, PA (US); Daneen K. Touhalisky, Downingtown, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 165 days.

This patent is subject to a terminal disclaimer.

(21) Appl. No.: 13/963,262

(22) Filed: Aug. 9, 2013

(65) Prior Publication Data

US 2013/0331845 A1  Dec. 12, 2013

Related U.S. Application Data

(63) Continuation of application No. 12/691,374, filed on Jan. 21, 2010, now Pat. No. 8,529,571.

(60) Provisional application No. 61/146,898, filed on Jan. 23, 2009.

(51) Int. Cl.
    *A61B 17/15*  (2006.01)
(52) U.S. Cl.
    CPC .............. *A61B 17/157* (2013.01); *A61B 17/15* (2013.01)

(58) Field of Classification Search
    CPC .... A61B 17/15; A61B 17/151; A61B 17/152; A61B 17/154; A61B 17/155; A61B 17/157; A61B 17/158
    See application file for complete search history.

(56) References Cited

U.S. PATENT DOCUMENTS

| 4,627,425 | A |   | 12/1986 | Reese |
|---|---|---|---|---|
| 4,718,414 | A |   | 1/1988 | Saunders et al. |
| 5,021,056 | A | * | 6/1991 | Hofmann et al. ........... 606/86 R |
| 5,364,402 | A |   | 11/1994 | Mumme et al. |
| 5,413,579 | A | * | 5/1995 | Tom Du Toit ................... 606/87 |
| 6,030,391 | A |   | 2/2000 | Brainard et al. |
| 7,141,053 | B2 | * | 11/2006 | Rosa et al. .................. 606/86 R |

(Continued)

FOREIGN PATENT DOCUMENTS

| EP | 0574656 A1 | 12/1993 |
|---|---|---|
| EP | 1275345 A2 | 1/2003 |

(Continued)

*Primary Examiner* — Anu Ramana
(74) *Attorney, Agent, or Firm* — Fay Kaplun & Marcin, LLP (57) ABSTRACT

An apparatus for locating a curvilinear cut in a bone comprises a jig body and a first arm, a top end of which is rotatably coupleable to a first portion of the jig body in combination with a second arm, a top end of which is rotatably coupleable to a second portion of the jig body separated from the first portion and a saw guide rotatably coupleable to the first arm, the saw guide including a bottom surface extending along a curve corresponding to a desired path through which a bone is to be cut, the saw guide including a locking feature receiving a bone fixation element which, in an operative configuration, is mounted in the bone to align the saw guide relative to the arm so that an operator may precisely align a desired axis of the saw guide with a longitudinal axis of the first arm.

20 Claims, 10 Drawing Sheets

(56) References Cited

U.S. PATENT DOCUMENTS

| | | | |
|---|---|---|---|
| 8,211,113 B2 * | 7/2012 | Brown et al. | 606/96 |
| 8,282,645 B2 * | 10/2012 | Lawrence et al. | 606/87 |
| 8,591,516 B2 * | 11/2013 | Metzger et al. | 606/88 |
| 2004/0236341 A1 | 11/2004 | Petersen | |
| 2008/0044244 A1 | 2/2008 | Keffer | |

FOREIGN PATENT DOCUMENTS

| | | |
|---|---|---|
| EP | 1464305 A2 | 10/2004 |
| JP | S61255650 | 11/1986 |
| JP | 2007-029657 | 2/2007 |

* cited by examiner

JIG AND SAW GUIDES FOR USE IN OSTEOTOMIES

PRIORITY INFORMATION

The present application is a Continuation application of U.S. patent application Ser. No. 12/691,374 filed Jan. 21, 2010, now U.S. Pat. No. 8,529,571; which claims priority of U.S. Provisional Patent Application Serial No. 61/146,898 filed Jan. 23, 2009. The disclosures of these applications and/or patents are incorporated herein by reference.

FIELD OF THE INVENTION

The invention relates generally to a jig and saw guide for bone fixation and, in particular, to a jig and saw guide for locating a curvilinear cut in a bone when performing tibial plateau leveling osteotomies.

BACKGROUND INFORMATION

Tibial Plateau Leveling Osteotomies ("TPLO"s) are performed on canines to stabilize the stifle joint after ruptures of the cranial cruciate ligament ("CCL"). Injuries of the CCL are among the most common canine orthopedic problems and are the cause of joint pain, muscle atrophy and decreased mobility often leading to hindlimb lameness and osteoarthritis. TPLOs employ instrumentation comprising a jig for locating a cut axis on a tibia. A saw is then manipulated to cut through the bone along the cut axis.

SUMMARY OF THE INVENTION

The present invention is directed to an apparatus for locating a curvilinear cut in a bone comprising a jig body and a first arm, a top end of which is rotatably coupleable to a first portion of the jig body in combination with a second arm, a top end of which is rotatably coupleable to a second portion of the jig body separated from the first portion and a saw guide rotatably coupleable to the first arm, the saw guide including a bottom surface extending along a curve corresponding to a desired path through which a bone is to be cut, the saw guide including a locking feature receiving a bone fixation element which, in an operative configuration, is mounted in the bone to align the saw guide relative to the aim so that an operator may precisely align a desired axis of the saw guide with a longitudinal axis of the first arm.

DETAILED DESCRIPTION

Figure 10:
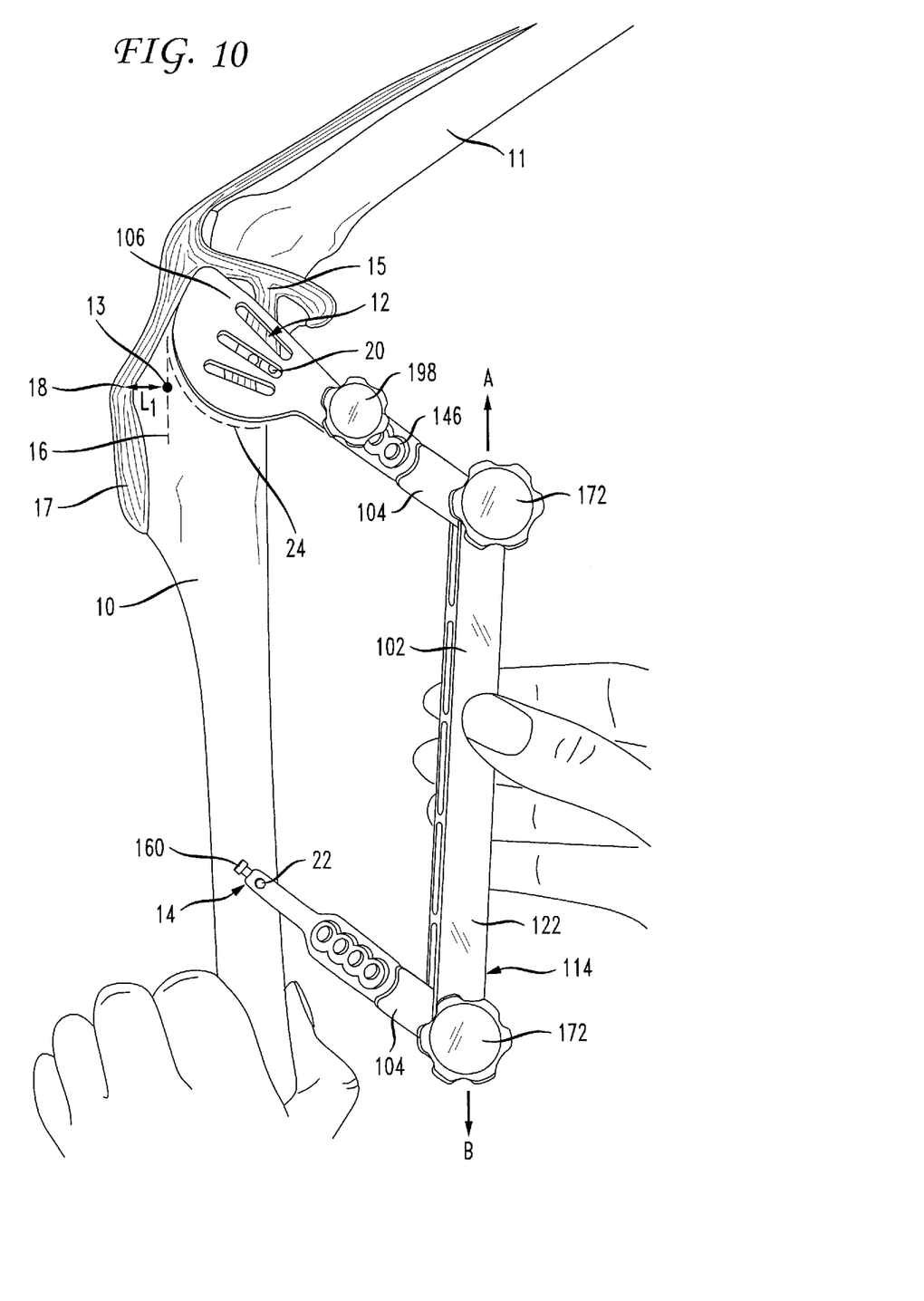
FIG. 10 shows the TPLO device of FIG. 1 positioned against a target bone.

The present invention may be further understood with reference to the following description and the appended drawings, wherein like elements are referred to with the same reference numerals. The present invention relates generally to methods and devices for the stabilization of joints. Specifically, the present invention relates to methods and devices for forming a curvilinear cut through the tibia of a stifle joint connecting the femur and tibia of a cat or dog in connection with a Tibial Plateau Leveling Osteotomy ("TPLO") procedure. However, as would be understood by those skilled in the art, the invention may be employed in conjunction with any bone fixation procedure for a human or another animal. Those skilled in the art will understand that, as used in this application, the term proximal refers to a direction approaching a joint of the targeted appendage with the canine torso while the term distal refers to the opposite direction—i.e., toward a paw of the appendage. The term medial refers to a direction approaching a sagittal plane of the canine while the term lateral refers to an opposite direction. Furthermore, in an operative position discussed in the present invention, a canine or other animal is positioned on an operating table resting on a lateral body surface. The term top in this application refers to a portion of the device proximate to a user thereof while bottom refers to portions of the device separated from the user—i.e., inserted into a animal on which the device is to be employed. It is further noted that directional terms assigned to components of the TPLO device of the present invention are labeled in accordance with a position of the TPLO device when in an operative configuration, as shown in FIG. 10 and described in greater detail below. However, those skilled in the art will understand that these terms are used to describe an exemplary procedure and are not intended to limit the invention. That is, the device may be oriented in other directions if so desired—e.g., when employed in different animals—as would be understood by those skilled in the art.

As shown in FIGS. 1-4, a TPLO device 100 according to an exemplary embodiment of the invention comprises a jig body 102 structured to mount arms 104 on ends thereof. As will be described in more detail below, the device 100 which is employed to guide the cutting of the tibia in a TPLO procedure, includes a pair of arms 104 which may be rotatably mounted on ends of the jig body 102. A free end of each of the arms 102 may be attached to a target portion of a tibia. The target positions to which the free ends of the arms 104 are fixed are selected so that a saw guide 106, when attached to the free end of a first one of the arms 104, extends over the head of the tibia in a desired position as will be described in more detail below. The saw guide 106 may be attached to the first aim 104 in a plurality of configurations which will be selected by a user of the device to locate a curvilinear cut axis through the head of the tibia so that the head of the cut portion of the tibia may be rotated therealong to level the tibial plateau as will be understood by those skilled in the art. Specifically, the present invention permits a user to position the saw guide 106 at a desired position and orientation on the TPLO device 100 after the TPLO device has been attached to the tibia, thus increasing the accuracy of the TPLO procedure. The saw guide 106 according to this embodiment may be attached to the TPLO device 100 in any of twelve configuration chosen to best suit the anatomical requirements of the procedure being performed. However, those skilled in the art will understand that the device 100 may be structured to permit any number of positions for the saw guide 106.

The TPLO device 100 of the present invention also helps to stabilize a saw blade and ensures a proper alignment against the tibia while performing a cut. Furthermore, the TPLO device 100 of the present invention may be employed with either a right tibia or a left tibia. Alternatively, the TPLO device 100 may be employed with another bone including, but not limited to the distal tibia, calcaneus, radius, ulna, humerus, femur or phalanx. Parts of the TPLO device 100, as described in greater detail below, may be formed of a substantially rigid material known in the art.

Figure 5A:
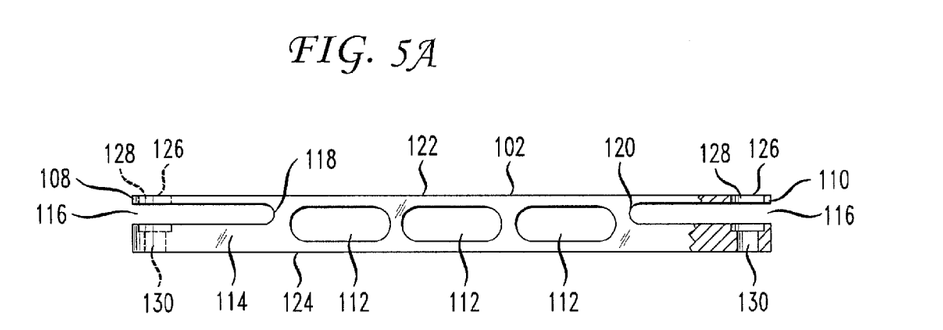
FIG. 5A shows a partial cut-through caudal view of a jig body according to the present invention.
Figure 5B:
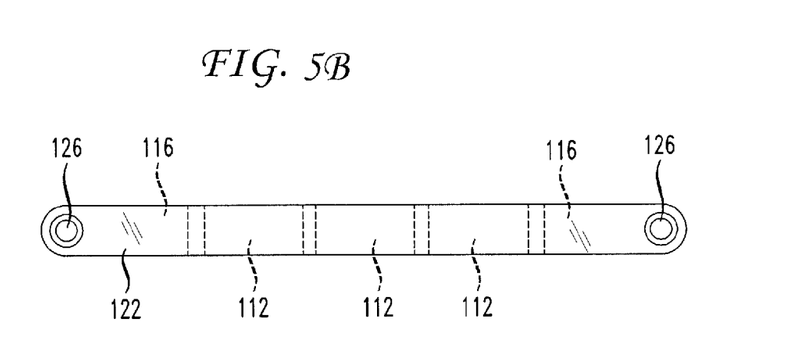
FIG. 5B shows a superior view of the jig body of FIG. 5A.

As shown in FIGS. 5A and 5B, the jig body 102 is an elongated member with ends 108 and 110. The jig body 102 has a substantially rectangular cross-section dimensioned to engage designated portions of a tibia in accordance with a standard TPLO procedure, as those skilled in the art will understand. That is, the jig body 102 is formed so that the aims 104 may be separated from one another by a distance required to properly stabilize the device 100 relative to the tibia as those skilled in the art will understand. To lighten the jig body 102 and to provide a indication of proper alignment of the device 100, a plurality of bores 112 extend therethrough in a direction substantially perpendicular to a longitudinal axis of the jig body 102 between the first end 108 and the second end 110. Although the bores 112 are shown formed with a substantially elliptical cross section, any shape and size of the bores 112 is envisioned in the exemplary embodiment. The bores 112 may be evenly disposed over a caudal face 114 of the jig body. Furthermore, any number of bores 112 may be employed without deviating from the spirit and scope of the present invention. For example, instead of three bores 112, the jig body 102 may comprise one bore dimensioned to cover a greater portion of the caudal face 114. In one embodiment of the present invention, the caudal face 114 is preferably oriented so that, when the device 100 is coupled to the tibia in a desired position, the caudal face 114 extends substantially perpendicular to a sagittal plane passing through the tibia. Thus, an observer viewing a lateral face 122 of the jig body 102 from a direction perpendicular to a sagittal plane can determine that the jig body 102 is out of alignment—i.e., coupled to the tibia in a plane not parallel to one of the sagittal plane and the patellar tendon—if the bores 112 are visible. In a second embodiment, the observer may view the jig body from a cranial side with a viewing angle in the cranial-caudal plane. In this manner, if either side wall of the bores 112 is visible, the observer will understand that the jig body 102 is misaligned. It is noted however, that alignment of the jig body 102 via the bores 112 is not a requirement of the TPLO device of the present invention. Specifically, alignment of the TPLO device 100 with the tibia can also be completed by visual inspection of a position of the TPLO device relative to one of the tibia and the patellar tendon as would be understood by those skilled in the art. The bores 112 described herein are an optional element which lighten the jig body 102 and which may optionally be used to double check the orientation of the jig body 102.

Figure 3:
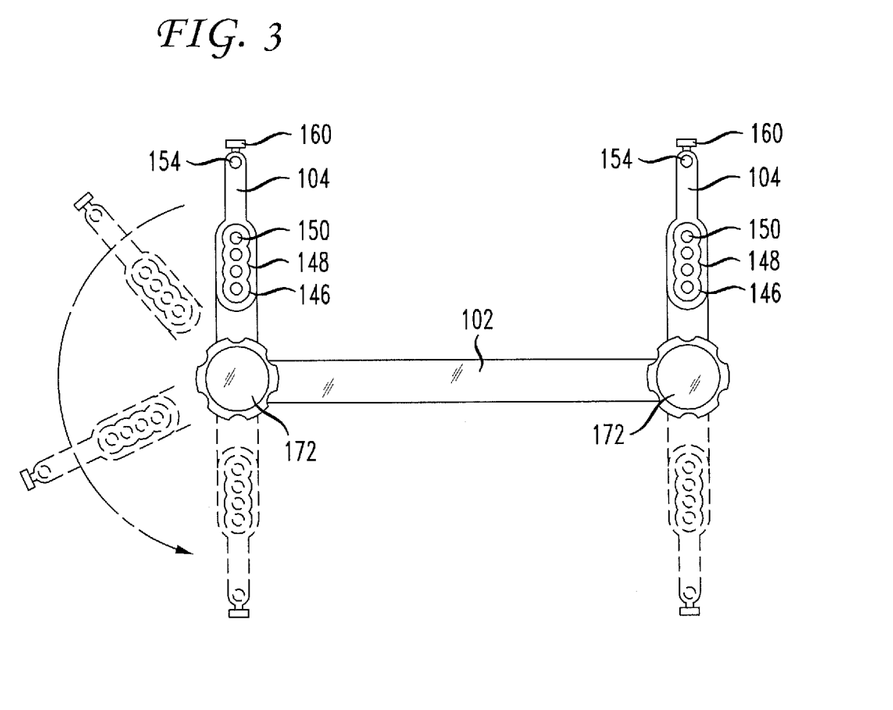
FIG. 3 shows a superior view of the TPLO device of FIG. 2.

First and second ends 108, 110 of the jig body 102 comprise slots 116 that each extend into the jig body 102 by a predetermined distance. Dimensions of each of the slots 116 are chosen to permit the arms 104 to rotate therethrough. A length of each of the slots 116 is selected to permit the second end of each of the arms 104 to rotate therethrough without contacting the ends 118 thereof, as shown in FIG. 3. Specifically, the slots 116 are dimensioned to optimize a clamping force exerted on the contacting portions of the arms 104. As shown in the caudal view of FIG. 5A, bores 126 extend through the jig body 102 at an angle substantially parallel to the caudal face 114 from the superior face 122 to an inferior face 124 of the jig body 102. Each of the bores 126 comprises a first non-threaded portion 128 and a second threaded portion 130 longitudinally separated from one another. The first non-threaded portion 128 extends a predetermined distance from the superior face 122 and comprises a diameter substantially equivalent to a diameter of a second shaft portion 178 of a hinge screw 172 to be inserted therein, as will be described in greater detail below. The second threaded portion 130 extends from the first non-threaded portion 128 to the inferior face 124 and has a diameter substantially equivalent to a diameter of threads 182 of the hinge screw 172. Specifically, the first non-threaded portion 128 extends to a depth beyond the slots 116 such that a portion of the first non-threaded portion 128 is located on superior and inferior sides of each of the slots 116, as shown in the embodiment of FIG. 5A. Threads of the second threaded portion 130 are sized and shaped to engage threads 182. In practice, caudal ends 132 of the arms 104 are positioned to lie within the slots 116 and the hinge screws 172 are screwed therethrough. Specifically, each of the caudal ends 132 of the arms 104 comprises a bore 134 extending therethrough substantially perpendicular to a plane of the arms 104, as will be described in greater detail hereinafter.

Figure 6A:
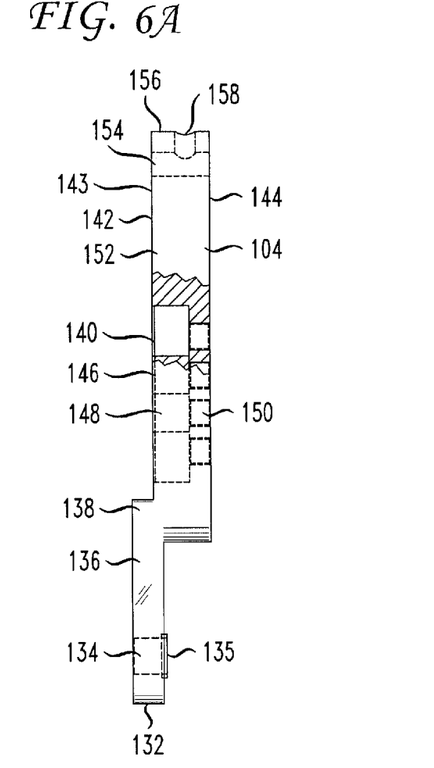
FIG. 6A shows a proximal view of an arm according to the present invention.
Figure 6B:
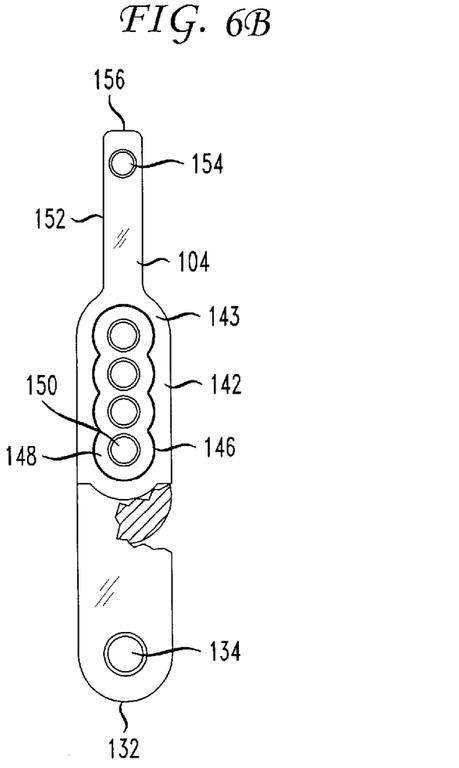
FIG. 6B shows a superior view of the side arm of FIG. 6A.
Figure 6C:
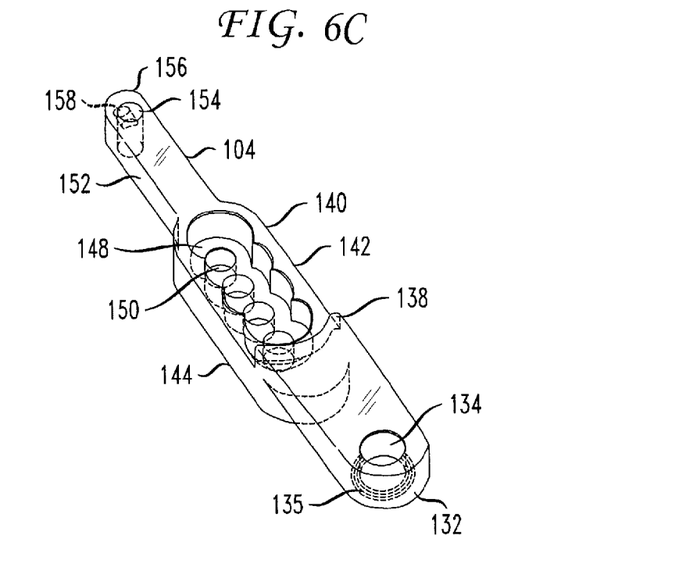
FIG. 6C shows a perspective view of the arm of FIG. 6A.

As shown in FIGS. 6A-6B, an arm 104 according to an exemplary embodiment of the invention includes a caudal portion 136 sized to be slidably received within the slot 116. It is noted that although these figures show only one aim 104, both of the arms 104 may be formed with the same dimensions and structure. The caudal portion 136 extends from the caudal end 132 to a ledge 138. In a preferred embodiment, a thickness of the caudal portion 136 may be substantially equivalent to a thickness of a respective one of the slots 116. The bore 134 is positioned adjacent the caudal end 132 such that the bore 134 is equidistant from edges of the arm 104, as shown in FIG. 6B. Specifically, the caudal end 132 is formed with a radius of curvature centered on a center of the bore 134 such that the caudal end 132 resembles a semi-circular shape. In this manner, when the arm 104 is situated within one of the slots 116, rotational movement of the arm 104 is permitted, as those skilled in the art will understand. The bore 134 is formed with a diameter substantially equivalent to a diameter of the first non-threaded portion 128 of the bores 126. In the alternate embodiment, if the first non-threaded portion 128 of each of the bores 126 is threaded, the bore 134 may also comprise similar threading. A rim of the bore 134 further comprises a diametric abutment 135 dimensioned to facilitate alignment with the bore 126 of the jig body 102 prior to insertion of the hinge screw 172. In one embodiment, the diametric abutment 135 may have a diameter greater than that of the bore 134 and substantially equivalent to a diameter of the first non-threaded portion 128 and may be dimensioned to retain the arm 104 in place within the bore 126 without a hinge screw 172.

The ledge 138 connects the caudal portion 136 to a cranial portion 140 of the arm 104. The cranial portion 140 lies in a plane parallel to a plane of the caudal portion 136 and is formed with a bottleneck shape where a shaft 142 lying adjacent to the ledge 138 tapers to a neck 152 at a cranial end 156 thereof. The shaft 142 further comprises a plurality of openings 146 extending through the shaft 140 from a superior face 143 to an inferior face 144 so that, when the device 100 is mounted on a tibia in a desired orientation, the openings 146 extend substantially perpendicular to the sagittal plane. The arm 104 according to this embodiment includes four openings 146 arranged along a longitudinal axis of the arm 104 with each opening being substantially circular overlapping a portion of an adjacent one of the openings 146. A superior portion 148 of each of the openings 146 has a first diameter and extends from the superior face 143 to a predetermined depth of the shaft 142 connecting to an inferior portion 150 of each of the openings 146. The inferior portion 150 opens to the inferior face 144. Each inferior portion 150 has a diameter smaller than the first diameter and is aligned with a respective one of the openings 146. Furthermore, because of their smaller diameter, the inferior portions 150 do not overlap one another and are separated from adjacent inferior portions 150 by a predetermined distance. Furthermore, the inferior portions 150 are threaded and have dimensions chosen to permit engagement with threads of a saw guide screw 198, as will be described in greater detail later on. It is noted that although the exemplary embodiment is discussed with four openings 146, any number of openings 146 may be employed without deviating from the spirit and scope of the present invention. Alternatively, the openings 146 and the thread holes 150 may be replaced by a slot which permits the selection of any position therein, as described in greater detail later on.

The neck 152 extends cranially beyond the shaft 142 by a predetermined distance and comprises a bore 154 at a cranial end portion thereof. The bore 154 is substantially cylindrical in shape and extends from the superior face 143 to the inferior face 144. The bore 154 is positioned adjacent a cranial end 156 of the arm 104 such that the bore 154 is equidistant from edges of the cranial end, as shown in FIG. 6B. Specifically, the cranial end 156 is formed with a radius of curvature centered on a center of the bore 156 such that the cranial end 156 resembles a semi-circular shape. In practice, the bore 154 may receive a bone attachment member (e.g., a pin) to attach the arm 104 to a target portion of bone, as will be described in greater detail with respect to an exemplary method of the present invention described later on. The cranial end 156 further comprises a through bore 158 extending into the arm 104 from the cranial end 156 substantially parallel to the longitudinal axis of the arm 104. The through bore 158 is substantially cylindrical and opens into the bore 154. In an alternate embodiment, the through bore 158 can extend into the arm 104 at any angle as long as a distal end thereof opens into the bore 154. As described in greater detail below, the through bore 158 receives a jig pin screw 160 to lockingly engage the bone attachment member inserted through the bore 154. In another embodiment of the present invention, another clamping means maybe used to secure the bone attachment member in place relative to the bore 154.

Figure 7A:
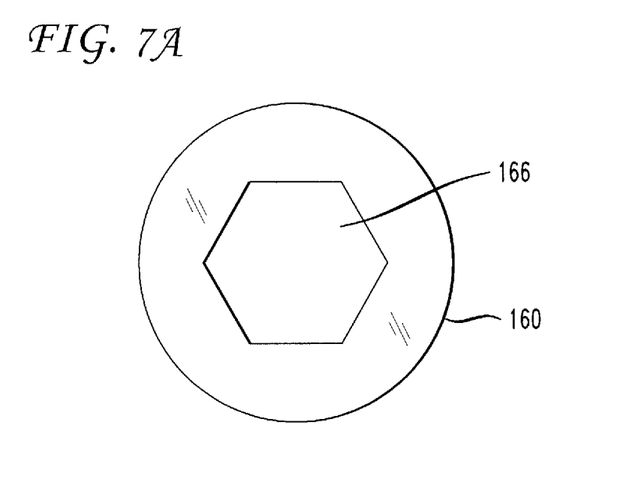
FIG. 7A shows a superior view of a jig pin screw according to the present invention.
Figure 7B:
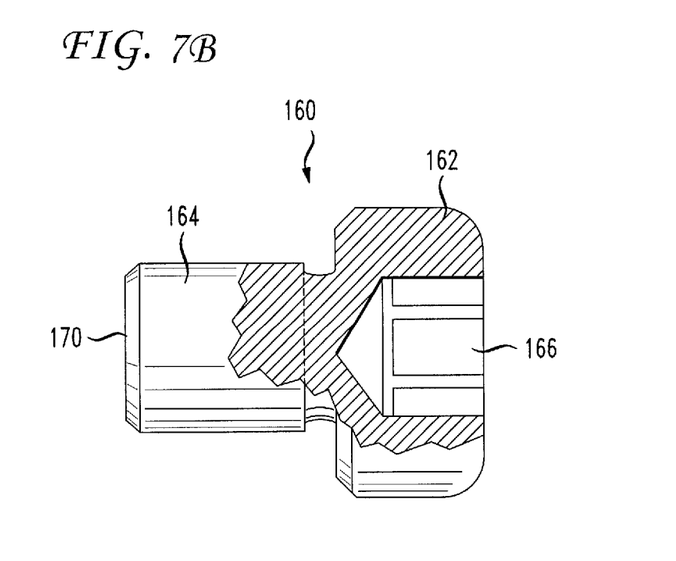
FIG. 7B shows a partial cut-through view of the jig pin screw of FIG. 7A.

FIGS. 7A-7B depict the exemplary jig pin screw 160 according to the present invention. The jig pin screw 160 comprises an increased diameter head 162 and a shaft 164. The head 162 comprises a hexagonal recess 166 to permit manipulation thereof by a respectively shaped driver, as those skilled in the art will understand. An end 170 of the shaft is substantially planar so that the jig pin screw 160 can apply a sufficient frictionally engaging pressure to the bone attachment member inserted in the bore 154.

Figure 4:
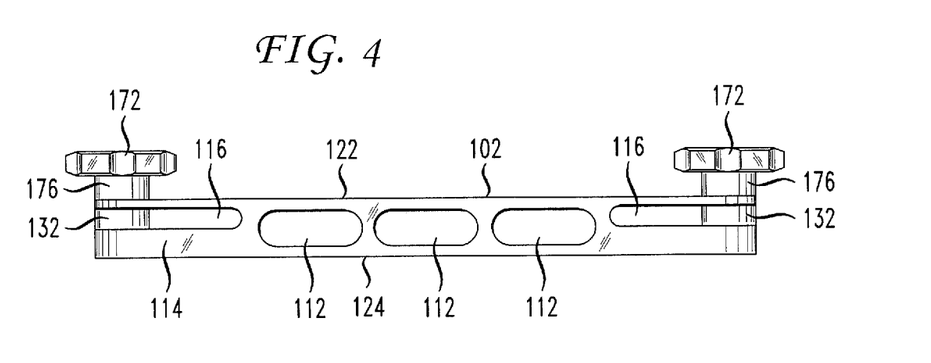
FIG. 4 shows a caudal view of the TPLO device of FIG. 1.
Figure 8A:
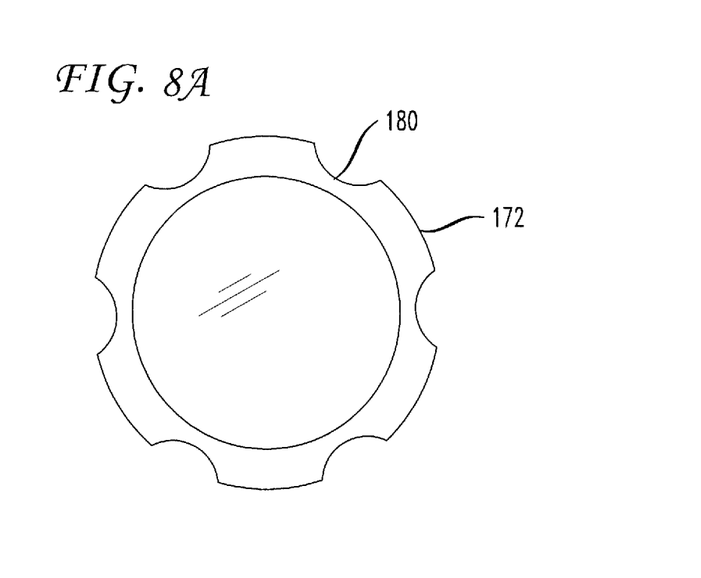
FIG. 8A shows a superior view of a hinge screw according to the present invention.
Figure 8B:
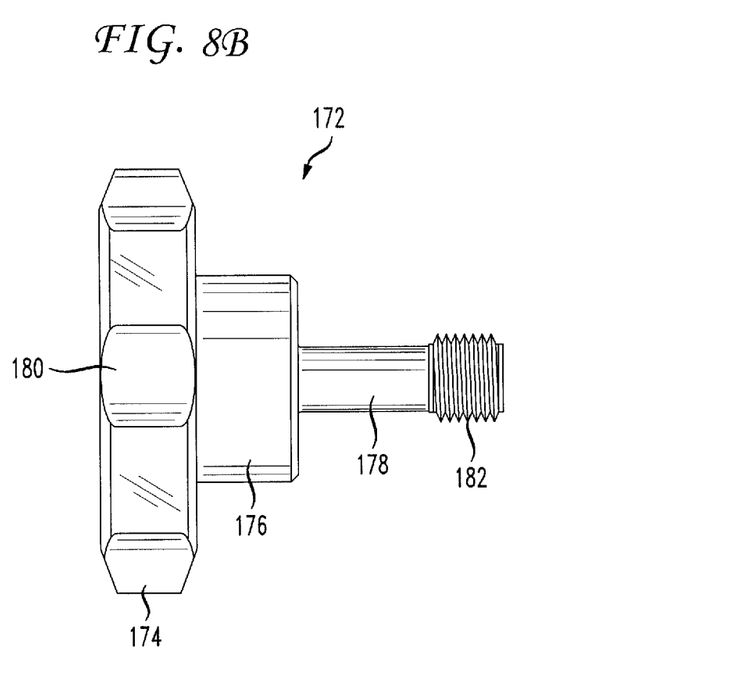
FIG. 8B shows a proximal view of the hinge screw of FIG. 8A.

FIGS. 8A-8B depict the exemplary hinge screw 172 according to the present invention. The hinge screw 172 comprises a head 174, a first shaft portion 176 and a second shaft portion 178. The head 174 is substantially circular and comprises a plurality of ergonomic grooves 180 disposed evenly about a circumference thereof to facilitate a manual manipulation thereof by a user. The first shaft portion 176 extends out of the head 174 and comprises a substantially cylindrical shape. A diameter of the first shaft portion 176 is greater than a diameter of the bore 154 such that, when inserted into the bore 154, the first shaft portion 176 rests on a portion of the superior face 122 bordering the bore 154, as shown in FIG. 4. The second shaft portion 178 extends distally of the first shaft portion 176 and comprises a diameter smaller than a diameter of the bore 154. A distal length of the second shaft portion comprises a plurality of threads 182 sized and shaped to engage the second threaded portion 130 of the bore 126, as will be described in greater detail later on.

Figure 1:
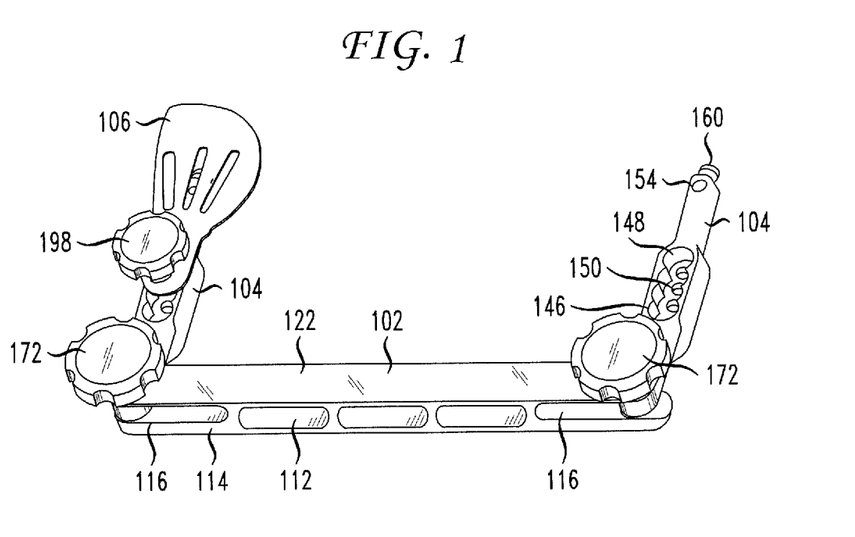
FIG. 1 shows a first perspective view of a TPLO device according to the present invention with a saw guide attached.
Figure 9A:
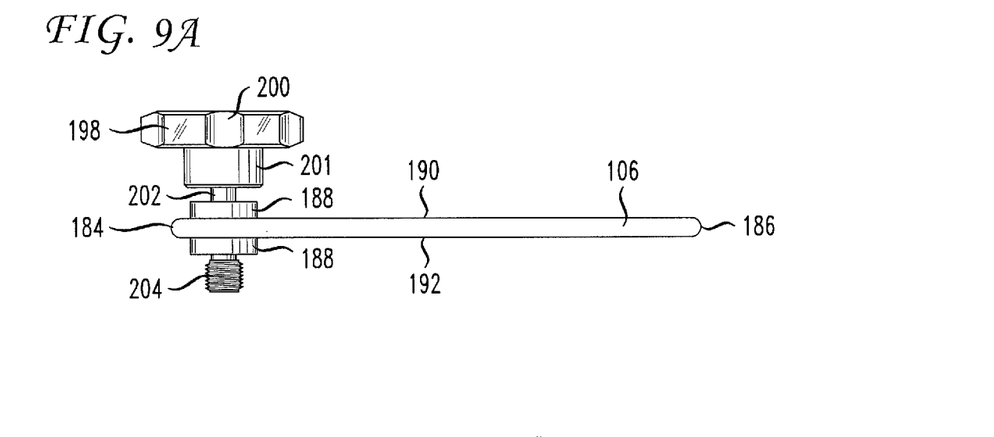
FIG. 9A shows a proximal view of a saw guide and saw guide screw according to the present invention.

As shown in FIGS. 1, 9A and 10, an exemplary saw guide screw 198 according to the present invention is formed substantially similarly to the hinge screw 172. The saw guide screw 198 is sized and shaped to lock the saw guide 106 in a selected one of the openings 146, wherein a threaded portion 204 of the saw guide screw 198 located on a distal end of a shaft 202 engages threads of the respective inferior portion 150 of the opening 146, as will be described in greater detail below. A head 200 of the saw guide screw 198 is also formed substantially similarly to the head 174 of the hinge screw 172.

Figure 9B:
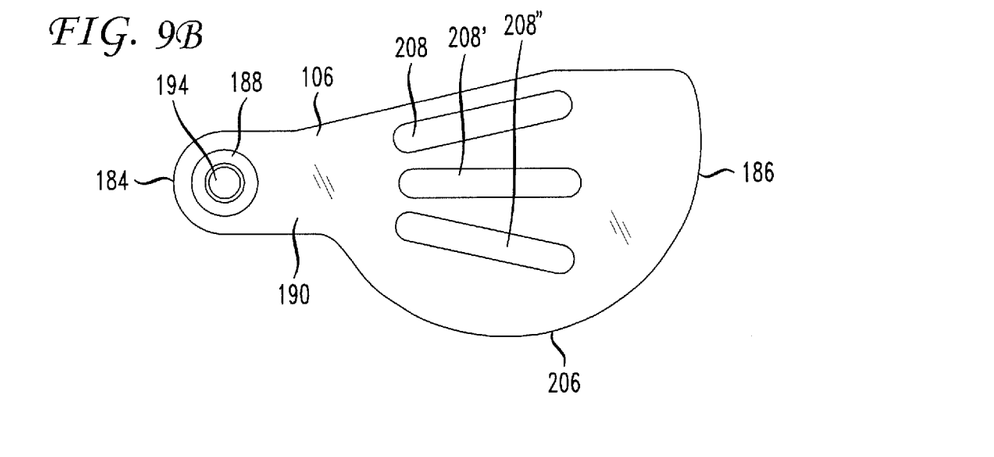
FIG. 9B shows a superior view of the saw guide of FIG. 9A.
Figure 9C:
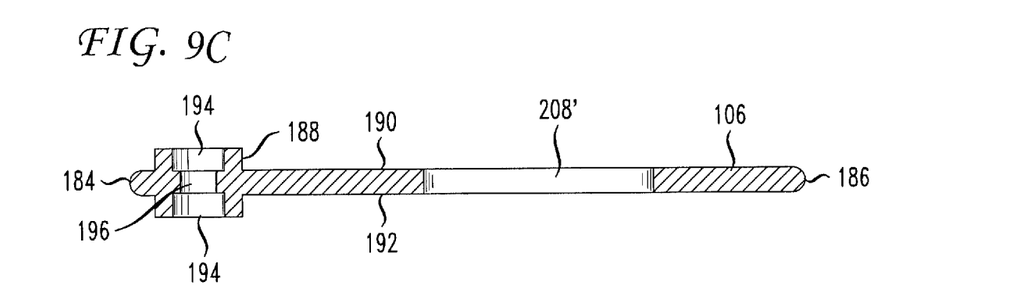
FIG. 9C shows a partial cross sectional view of the saw guide of FIG. 9A.

FIGS. 9A-9C depict an exemplary saw guide 106 according to the present invention. The saw guide 106 is formed with a shape resembling that of a fan blade, with a first caudal end 184 rounded along a first radius of curvature and a second cranial end 186 comprising a second radius of curvature, as those skilled in the art will understand. The caudal end 184 further comprises an abutment 188 extending out of a plane of the saw guide 106 in a direction substantially perpendicular thereto. Specifically, the abutment 188 extends out of a superior face 190 and an inferior face 192 by the same predetermined distance. The abutment 188 is substantially cylindrical in shape and is sized to frictionally engage the superior portion 148 of one of the openings 146. The abutment 188 further comprises a bore 194 extending perpendicularly therethrough. The bore 194 is sized and shaped to permit the saw guide screw 184 to be inserted therethrough to lockingly engage one of the inferior portions 150 of the openings 146, as will be described in greater detail hereinafter, A reduced diameter portion 196 of the bore 194 that lies in the same plane as a plane of the saw guide comprises a diameter smaller than a diameter of the bore and, in an exemplary embodiment, is sized to frictionally engage the shaft 202 of the saw guide screw 198. The bore 194 is centered adjacent the proximal end 184 such that the bore 194 is equidistant from edges thereof.

The cranial end 186 is formed with a predetermined radius of curvature defining a curvature of the saw guide 106 along a first side 206. The first side 206 has an arc length of approximately 90° and a radius of, for example, 24 mm., 27 mm. or 30 mm. The selected radius of curvature may be selected to locate a curvilinear cut axis in a tibia of a canine as would be understood by those skilled in the art. Specifically, the anatomy of the tibia, which varies by breed, as well as placement position of the TPLO device 100 may affect a required radius of curvature of the saw guide 106. Thus, a veterinarian or other user of the device may select an appropriately sized saw guide 106 after attachment of the TPLO device to the tibia. One such alternate embodiment is discussed later on with respect to FIG. 11.

The saw guide 106 also comprises a plurality of slots, each of which defines a different longitudinal axis. Specifically, the saw guide 106 may comprise three slots 208, 208' and 208". The slot 208' may be oriented along a longitudinal axis substantially parallel to a longitudinal axis of the saw guide 106 while longitudinal axes of the slots 208 and 208" deviate therefrom, for example, at equal and opposite angles enabling a user to select a desired orientation of the saw guide 106 to properly place the cut in the tibia. In one example, the slot 208 may deviate from a longitudinal axis of the slot 208' by an angle of −13° while the slot 208" may deflect by an angle of +13°. Each of the slots 208, 208' and 208" has substantially the same dimensions, which are chosen to permit alignment with an axis defined by the bone attachment member and the jig pin screw 160, as will be described in greater detail below. In an alternate embodiment, the slots 208, 208' and 208" can take any other desired shape such as, for example, a circular hole or markings formed on the superior face 190 of the saw guide 106.

Figure 2:
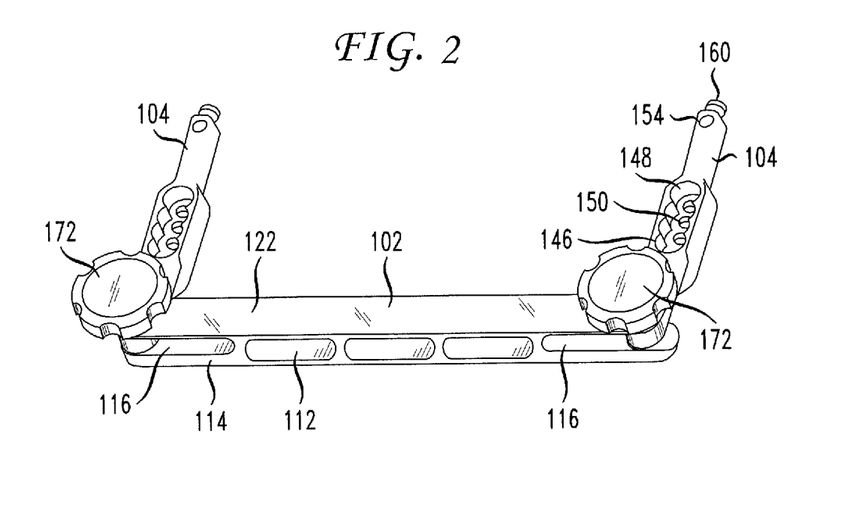
FIG. 2 shows a second perspective view of the TPLO device of FIG. 1 without a saw guide.

As shown in FIG. 10, an exemplary method according to the present invention begins with the assembly of the TPLO device 100 in a desired configuration as shown in FIGS. 2-4. Prior to initiating a TPLO procedure, arms 104 of the TPLO device 100 are assembled such that the jig pin screws 160 sit loosely within the through bores 158. In this position, the bores 154 remain substantially unobstructed by ends of the jig pin screws 160. The aims 104 are then inserted into the slots 116 and the hinge screws 172 are loosely positioned in the bores 126 so that the arms 104 are rotatable with respect to the jig body 102, as shown in FIG. 3. In an exemplary embodiment, the arms 104 can rotate by at least 240° relative to the jig body 102 to accommodate attachment of the TPLO device 100 to one of the right and left limbs without having to flip the TPLO device 100 over.

The TPLO device 100 is then positioned adjacent the tibia such that the jig body 102 is parallel to a sagittal plane of the animal. A first hole 12 is drilled in the condyle of the tibia 10 adjacent the tibial plateau. Specifically, the first hole 12 is drilled approximately 3-4 mm distally of a joint surface between the tibia 10 and femur 11, caudal to the medial collateral ligament 15, as those skilled in the art will understand. A second hole 14 is then drilled into the tibia 10 at a position approximately midway along the longitudinal length thereof, as would be understood by those of skill in the art.

Bone pins 20, 22 are then inserted into a respective one of the first and second holes 12, 14 at angles substantially perpendicular to a longitudinal axis of the tibia, as those skilled in the art will understand. To overcome difficulties in alignment of the bone pins 20, 22 relative to the curved tibial surface, the bone pins 20, 22 are preferably aligned to be substantially perpendicular to a patellar tendon 17, which extends substantially along the proximal-distal axis on the cranial side of the tibia 10, as those skilled in the art will understand. Each the of bone pins 20 and 22 is substantially parallel to the other to permit an engagement with the bores 154 of the TPLO device 100. The TPLO device 100 is inserted over the bone pins 20, 22 such that each of the bores 154 of the arms 104 receives one of the bone pins 20, 22 therethrough. The TPLO device 100 is positioned substantially parallel to a plane defined by the tibia 10. Specifically, a user of the TPLO device 100 may position the TPLO device 100 such that the bores 112 and slots 116 extending through caudal and cranial faces of the jig body 102 are not visible from a superior-inferior viewing angle to confirm that the TPLO device 100 is parallel to a sagittal plane of the tibia 10. In a perfectly parallel configuration, cranial and caudal faces of the jig body 102 should not be visible at all from this viewing angle. The jig pin screws 160 may then be tightened in the through bores 158 to lock the TPLO device 100 in the parallel configuration. Specifically, a driver (not shown) with a hexagonally shaped tip may be used to transmit torque to screw the jig pin screws 160 into the through bores 158. Once tightened, ends 170 of the jig pin screws 160 may apply a frictionally engaging pressure to the bone pins 20, 22. Portions of the bone pins 20, 22 protruding out of the TPLO device 100 in a superior direction may then be cut, leaving only a desired length thereof protruding from the superior faces 143 of the arms 104.

The saw guide 106, selected in accordance with the method disclosed below, may then be attached at a desired position to the end of the arm 104 adjacent to the head of the tibia 10. The saw guide 106 must be positioned such that a center of rotation of the saw guide 106 is aligned with a center of rotation of the stifle joint of the animal, while maximizing the size of the tibial crest remnant. Specifically, a veterinarian or other user of the TPLO device 100 must choose a saw guide 106 that, when attached to the TPLO device 100 to designate a curvilinear cut 24, will leave no less than a predetermined width of the tibia at its narrowest point along the cranial-caudal plane. The dimensions of the tibia 10 of the animal may affect the required position of the saw guide 106. Specifically, as shown in FIG. 10, a cutting point 13 may be marked on the tibia 10 at a first length $L_1$ of at least 10 mm. lateral of a tibial tuberosity 18. The cutting point 13 defines a longitudinal axis 16 extending therethrough and along the tibia 10 at an angle parallel to the sagittal plane of the animal. The longitudinal axis 16 designates the portion of the tibia 10 that should remain uncut. Accordingly, the curvilinear, cut 24 should, at the most, come into contact with the longitudinal axis 16 without crossing therepast. A user of the TPLO device 100 may then select a saw guide 106 that provides a curvilinear cut 24 conforming to this requirement and attach the saw guide to a selected opening 146 by loosely screwing the saw guide screw 198 thereover. Specifically, a user of the TPLO device 100 can position the abutment 188 of the saw guide 106 over one of the four openings 146 so that the curvilinear cut 24 conforms to the requirements discussed above. Selection of an opening 146 may also be affected by a position of the bone pin 20 and the dimensions of the tibia 10, which, as noted earlier, vary, for example, by breed of the dog, etc. A first loose engagement of the saw guide 106 with the aim 104 permits a degree of flexibility with respect to saw guide positioning even after the bone pin 20 has been inserted into the head of the tibia 10.

The user of the TPLO device may select one of the slots 208, 208' and 208" to receive the bone pin 20 therethrough. This selection adjusts the rotation of the saw guide 106 about the saw guide screw 198 to a desired position. While the openings 146 on the arm 104 affect the location of a center of rotation of the curvilinear cut 24 along the aim 104. The TPLO device 100 of the present invention permits a user to position the saw guide 106 in one of twelve different positions against the tibia 10 once the bone pins 20, 22 have been inserted into the tibia 10, thus permitting a greater degree of precision in the TPLO procedure than presently available. Once an opening 146 and slot 208, 208' or 208" has been selected, the saw guide screw 198 is tightened into the selected opening 146 such that engagement of a first shaft portion 201 with the abutment 188 locks the saw guide 106 against the arm 104, thus preventing inadvertent movement thereof This tightening further permits the threaded portion 204 of the shaft 202 to engage the threaded inferior portion 150 of the opening 146.

Once the saw guide 106 has been locked against rotation, the jig body 102 may be maneuvered to further change the position of the saw guide 106. Specifically, the jig body 102 may be moved in directions A and B corresponding to proximal and distal directions of the tibia 10. The proximal and distal movement of the jig body 102 allows the selected slot to move relative to the bone pin 20. A user may then select a position of the jig body 102 that will produce the desired osteotomy position, as those skilled in the art will understand. Once properly positioned, the hinge screw 172 may be tightened to lock the jig body 102 against movement with respect to the arms 104. Specifically, threads 182 of the hinge screw 172 may be screwed into the second threaded portion 130 of the bore 126 until the first shaft portion 176 comes into engagement with the anterior face 122.

Figure 11:
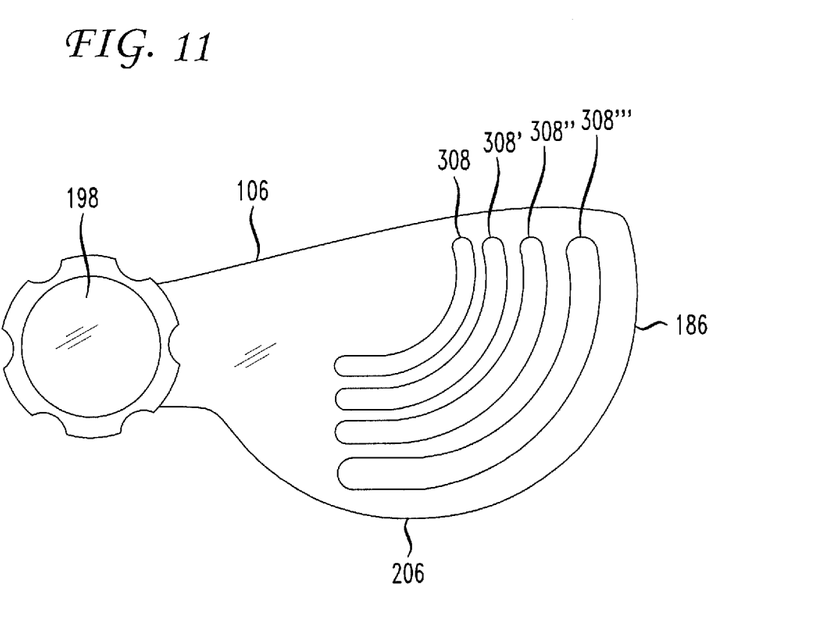
FIG. 11 shows an first alternate embodiment of the saw guide according to the present invention.

In an alternate embodiment of the present invention, as shown in FIG. 11, the slots 208 can assume any other shape on the saw guide 206. Specifically, the slots 308, 308', 308" and 308'" can be formed in an arced shape where a curvature of each one of the 308, 308', 308" and 308'" matches a curvature of the second distal end 186. According to an exemplary method of the present invention, once the saw guide 106 is positioned on the arm 104, the saw guide may be rotated so that one of the arced slots 308, 308', 308" and 308'" assumes a desired position relative to can thus be used as an aid in positioning the saw guide 106. Specifically, one of the slots 308, 308', 308" and 308'" can be positioned adjacent the bone pin 20, wherein the selected one of the slots 308, 308', 308" and 308' depends on which of the openings 146 of the arm 104 the saw guide 106 is attached to. The saw guide 106 is thus provided with a number of slots 308, 308', 308" and 308' corresponding to the number of openings 146 provided on the arm 104. A space between each of the slots 308, 308', 308" and 308'" is thus chosen to be substantially equivalent to a longitudinal space between a center of each one of the openings 146. The saw guide 106 is positioned such that the bone pin 20 is visible through a selected one of the slots 308, 308', 308" and 308'. Once properly positioned, the saw guide 106 may be locked in position as described above.

As will be understood by those skilled in the art, any known suitable saw blade with dimensions corresponding to the selected saw guide 106 may then be positioned over the saw guide 106 to perform an intermediate cut along the curvilinear cut line 24. The saw blade may rotate at an angle of ±10° with respect to the saw guide 106 to permit sufficient cutting of the bone without having to reposition the saw guide 106. In the intermediate cut, the saw blade (not shown) may penetrate only a portion of the tibia 10 at the designated cut area, the saw blade extending into the bone at an angle substantially perpendicular to a plane of the tibia 10. The exemplary embodiment of the present invention provides that the saw guide 106 is positioned in a plane parallel to a plane of the tibia 10. The saw blade (not shown) is positioned perpendicularly to the saw guide 106, thus overcoming the issue of locating a perpendicular plane relative to the non-planar head of the tibia, as those skilled in the art will understand. Once the intermediate cut has been made, a user may use a surgical marker to make markings at multiple locations along the curvilinear cut to aid in the location of the original alignment of the tibia 10 when performing latter steps of the osteotomy, as those skilled in the art will understand. Once the markings have been made, the saw blade (not shown) can complete the cut through the tibia 10 to complete the osteotomy procedure.

Although the present invention has been described with certain feature, it is noted that embodiments of the present invention may be modified in a plurality of ways without deviating from the spirit and scope of the present invention. For example, the saw guide 106 can assume any dimension suited to an animal and bone being treated. Specifically, the lateral side 206 of the saw guide 106 may have an arc length of a radius of 12 mm., 15 mm., 18 mm., 21 mm. or another radius suited to the requirements of the procedure. Similarly, positions, quantities and sizes of the openings 146 can also be varied to accommodate the requirements of a specific procedure. Furthermore, instead of multiple openings 146, a single leadscrew may be used, the leadscrew permitting a user to selectively position the saw guide 106 over a portion thereof, as those skilled in the art will understand.

In another embodiment, the bores 112 can be replaced by markings on the caudal face 114. The marking may then serve as indicators of proper parallel alignment with the plane of the tibia in the same way that the bores 112 do. The markings may be laser lines, machined etchings, etc.

In another alternate embodiment, the saw guide 106 can assume any shape instead of the fan blade shape shown. The saw guide 106 may be formed with straight edges to permit a straight planar cut into a bone or an angled edge to permit an angled cut into the bone, dimensions of the edges being chosen to conform to the requirements for a procedure in question.

In another embodiment, a drill guide may be used in place of the saw guide 106. The drill guide may be formed of any shape and size and can include a bore extending therethrough at a predetermined angle. Once positioned over the target area, a drilling member may be inserted into the bore of the drill guide to drill a hole through the target area. The drill guide can thus ensure that the hole is drilled at a precise predetermined angle with respect to a plane of the bone. In one example, the drill guide may be formed to ensure that a bore is perfectly perpendicular to a sagittal plane of the bone.

Figure 12A:
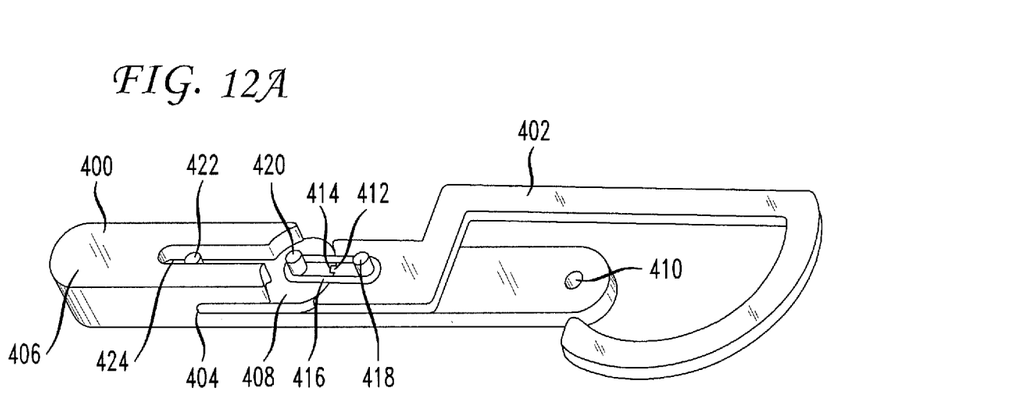
FIG. 12A shows a partial cut-through perspective view of a second alternate embodiment of the arm and saw guide according to the present invention.
Figure 12B:
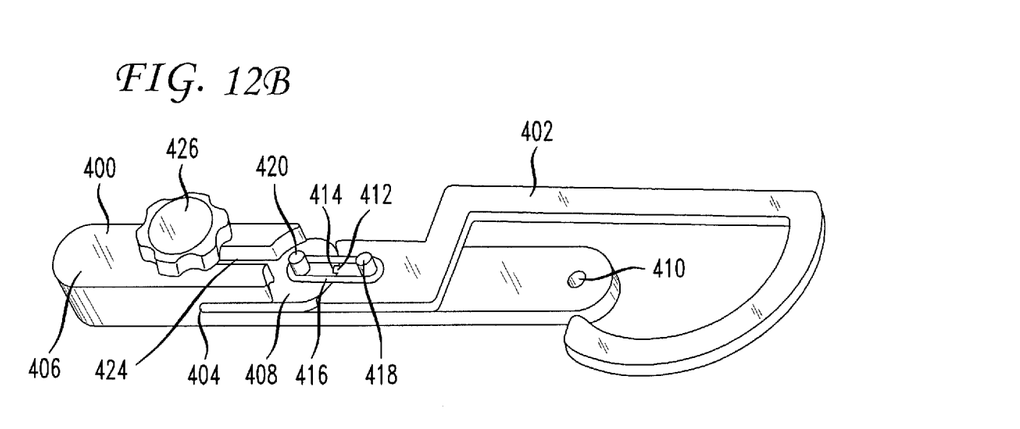
FIG. 12B shows another partial cut-through perspective view of the embodiment of FIG. 12A with a locking mechanism.

As shown in the partial cut-through view of FIGS. 12A and 12B, in yet another embodiment of the present invention, a saw guide 402 may be coupled to an arm 400. The saw guide 402 is formed with a fan-blade shape substantially following a profile of the saw guide 106 of FIG. 1. The arm 400 is dimensioned substantially similarly to the arm 104 of FIG. 1 and further comprises a slot 404 extending therethrough a predetermined distance from a cranial end. The slot 404 extends along a plane substantially parallel to a plane of a lateral face 406 of the arm 400 and is dimensioned to rotatably house the saw guide 402 therein. The saw guide 402 is connected at a caudal end to a rotatable element 408, which is further rotatably attached to a caudal portion of the arm 400 to permit rotation by at least 180° relative thereto. A saw guide with the dimensions required for a TPLO procedure may then be selected and attached to the arm 400. Specifically, the saw guide 402 may be formed with an arc length of approximately 90° and a radius of, for example, 24 mm., 27 mm. or 30 mm. A caudal end of the saw guide 402 comprises a tab 412 extending therefrom by a predetermined distance to engage a corresponding slot 414 formed in the rotatable element 408. The saw guide 402 may be locked in place via a connector 416 which is slidably received over protrusions 418, 420 formed on the saw guide 402 and rotatable element 408, respectively. Once locked to the rotatable element 408, the saw guide 402 and the rotatable element 408 are permitted to move in unison.

In operation, the arm 400 is first attached to the bone via a bone pin inserted through a bore 410 formed on a cranial end of the 400. In an insertion configuration, the saw guide 402 is locked against movement relative to the arm 400. Specifically, in the locked configuration, the rotatable element 408 is moved to a caudal-most position in the slot 404 such that protrusions 420 and 422 formed on a lateral face thereof engage a slot 424 formed on the lateral face 410 of the arm. Once properly positioned, the saw guide 402 may manually be moved cranially by a distance at least sufficient to permit the protrusion 420 to move cranially out of the slot 424. The saw guide 402 may be moved further cranially to affect a location of the curvilinear cut axis, similar to how the openings 146 are employed in the first embodiment disclosed earlier. The saw guide 402 may then be rotated by a required angle to further define an orientation of the curvilinear cut axis, as also described in greater detail earlier. As shown in FIG. 12B, in one embodiment, the protrusion 422 may further comprise a locking screw 426 formed thereover to permit locking of the saw guide 402 to the desired position. The locking screw 426 is formed substantially similar to the hinge screw 172 of FIG. 1. Once the saw guide 402 has been properly positioned, the locking screw 426 may be tightened, the tightening force causing a constriction of the rotatable element 408 within the slot 404, thus preventing a rotation thereof.

It will be apparent to those skilled in the art that various other modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. An apparatus for locating a curvilinear cut in a bone, the apparatus comprising:
   a jig body;
   a first arm, a top end of which is coupleable to a first portion of the jig body; and
   a saw guide rotatably coupleable to the first arm, the saw guide including a bottom surface extending along a curve, which, when the apparatus is in a desired position relative to a target portion of bone, corresponds to a desired path along which a saw is to be guided to cut the target portion of bone.

2. The apparatus of claim 1, further comprising a second arm, a top end of which is coupleable to a second portion of the jig body separated from the first portion.

3. The apparatus of claim 2, wherein top ends of the first and second arms are slidably received in slots separated from one another along a length of the jig body.

4. The apparatus of claim 2, wherein the first and second arms are rotatably coupleable to the jig body.

5. The apparatus of claim 1, wherein the jig body includes an orientation feature formed flush to a surface which, when the jig body is coupled to a bone in a desired orientation, extends in a plane substantially perpendicular to a plane including first and second axes along which the first and second arms, respectively, extend from the jig body, the orientation feature being formed as an opening in the surface substantially perpendicular to the plane within which the first and second arms extend from the jig body.

6. The apparatus of claim 1, wherein the first arm includes a series of mounting positions at which the saw guide may be rotatably coupled thereto, the mounting positions being separated from one another along the longitudinal axis of the first arm.

7. The apparatus of claim 1, wherein the saw guide includes a locking feature receiving a bone fixation element which, in an operative configuration, is mounted in the bone to align the saw guide relative to a longitudinal axis of the first arm.

8. The apparatus of claim 7, wherein the locking feature includes a plurality of openings extending through the saw guide, each of the openings extending along a corresponding one of a plurality of axes of the saw guide.

9. The apparatus of claim 8, wherein a bottom end of the first arm includes a bore extending perpendicularly into the plane including the first and second axes along which the first and second arms extend from the jig body, the bore receiving the bone fixation element to couple the apparatus to the bone so that the bone fixation element, when in the operative configuration, passes through the bore and then through a selected one of the openings of the locking feature to lock the saw guide in a desired orientation relative to the first arm.

10. The apparatus of claim 8, wherein the bottom end of the first arm further comprises a bone fixation element locking hole open to the bore so that a locking element inserted into the bone fixation element locking hole engages a bone fixation element inserted through the bore to lock the first arm to the bone fixation element.

11. An apparatus for locating a curvilinear cut in a bone, the apparatus comprising:
    a jig body; and
    a saw guide movably coupleable to the jig body, the saw guide including a bottom surface extending along a curve, transitioning into a side wall thereof, and ending at a top surface thereof, the curve corresponding to a desired path along which a saw is guided to cut a target portion of bone.

12. The apparatus of claim 11, wherein the saw guide includes a locking feature receiving a bone fixation element which, in an operative configuration, is mounted in the bone to align the saw guide relative to a longitudinal axis of the first arm, the locking feature including a plurality of openings extending through the saw guide, each of the openings extending along a corresponding one of a plurality of axes of the saw guide.

13. The apparatus of claim 11, further comprising a first arm connecting the jig body to the saw guide, a top end of the first arm being rotatably coupleable to a first portion of the jig body.

14. The apparatus of claim 13, wherein the first arm includes a series of mounting positions at which the saw guide may be rotatably coupled thereto, the mounting positions being separated from one another along the longitudinal axis of the first arm.

15. The apparatus of claim 13, wherein a bottom end of the first arm includes a bore extending perpendicularly into the plane including the first and second axes along which the first and second arms extend from the jig body, the bore receiving the bone fixation element to couple the apparatus to the bone so that the bone fixation element, when in the operative configuration, passes through the bore and then through a selected one of the openings of the locking feature to lock the saw guide in a desired orientation relative to the first arm.

16. The apparatus of claim 13, further comprising a second arm, a top end of which is rotatably coupleable to a second portion of the jig body separated from the first portion.

17. The apparatus of claim 16, wherein the jig body includes an orientation feature formed flush to a surface which, when the jig body is coupled to the bone in a desired orientation, extends in a plane substantially perpendicular to a plane within which the first and second arms extend from the jig body.

18. The apparatus of claim 17, wherein the orientation feature is an opening in the surface substantially perpendicular to the plane including the first and second axes along which the first and second arms extend from the jig body.

19. The apparatus of claim 16, wherein top ends of the first and second arms are slidably received in slots separated from one another along a length of the jig body.

20. An apparatus for locating a curvilinear cut in a bone, the apparatus comprising:
- a first arm removably attachable to a jig body; and
- a saw guide removably coupleable to the first arm, the saw guide including a bottom surface extending along a curve, the curve corresponding to a desired path along which a saw is guided to cut a target portion of bone, the saw guide being rotatable relative to the first arm so that an operator may precisely align a desired axis of the saw guide with a longitudinal axis of the first arm to define a corresponding cut in the bone.

* * * * *